United States Patent [19]

Jankun et al.

[11] Patent Number: 5,679,350
[45] Date of Patent: Oct. 21, 1997

[54] METHOD OF DELIVERY OF A MEDICAMENT TO A CANCER CELL USING A PATHWAY OF PLASMINOGEN ACTIVATOR MATERIAL

[75] Inventors: Jerzy Jankun, Sylvania, Ohio; Richard Hart, Greenwich, Conn.

[73] Assignee: The University of Toledo, Toledo, Ohio

[21] Appl. No.: 646,561

[22] Filed: May 8, 1996

Related U.S. Application Data

[63] Continuation of Ser. No. 294,950, Aug. 24, 1994, abandoned, which is a continuation-in-part of Ser. No. 59,813, May 10, 1993, abandoned, which is a continuation-in-part of Ser. No. 889,783, May 28, 1992, abandoned.

[51] Int. Cl.[6] ............................... A61K 39/385
[52] U.S. Cl. ..................... 424/193.1; 424/197.11; 424/542; 435/326; 435/346
[58] Field of Search ............... 424/193.1, 197.11, 424/196.11, 542; 435/240.26, 240.27, 326, 346

[56] References Cited

U.S. PATENT DOCUMENTS

| | | | |
|---|---|---|---|
| 4,923,807 | 5/1990 | Webb et al. | 435/69.2 |
| 5,087,616 | 2/1992 | Myers et al. | 514/21 |
| 5,112,606 | 5/1992 | Shiosaka et al. | 530/389.2 |
| 5,260,191 | 11/1993 | Yong | 435/6 |
| 5,519,120 | 5/1996 | Dano et al. | 530/388.22 |
| 5,532,132 | 7/1996 | Wang et al. | 435/7.21 |

FOREIGN PATENT DOCUMENTS 9012091  10/1990  WIPO.

OTHER PUBLICATIONS

Cubellis, M.V. et al., "The Embo Journal," vol. 9, #4, 1990, pp. 1079–1085.

*Primary Examiner*—Leon B. Lankford, Jr.
*Assistant Examiner*—Christopher R. Tate
*Attorney, Agent, or Firm*—Brinks Hofer Gilson & Lione

[57] ABSTRACT

A method of delivering a medicament to the surface of a cancer cell and transferring the medicament into the cancer cell using an activated plasminogen activator material such as a plasminogen activator inhibitor type-1 or type-2 (PAI-1, PAI-2). The medicament is coupled to PAI-1 or PAI-2 to form a reaction product that is coupled with the urokinase plasminogen activator (uPA) that is bound to the cell surface by the uPA receptor (uPAR). The medicament is coupled to PAI-1 or PAI-2 (for example, using a preserving agent such as saporin) in such a way that the medicament does not interfere with active sites responsible for binding to uPA or LRP proteins responsible for the internalization of the plasminogen activator material/conjugated medicament. The conjugated medicament prevents the conversion of the plasminogen activator inhibitor material into its latent inactive form. The resulting complex is internalized into the cancer cell to deliver the medicament within the cell.

17 Claims, No Drawings

METHOD OF DELIVERY OF A MEDICAMENT TO A CANCER CELL USING A PATHWAY OF PLASMINOGEN ACTIVATOR MATERIAL

This application is a continuation of application Ser. No. 08/294,950 filed on Aug. 24, 1994, now abandoned, which is a continuation-in-part application of application Ser. No. 08/059,813 filed May 10, 1993 now abandoned which is a continuation-in-part of application Ser. No. 07/889,783 filed May 28, 1992 now abandoned.

FIELD OF INVENTION

The present invention deals with novel methods of selective delivery of anticancer medicaments into tumor cells using an active plasminogen activator material such as active plasminogen activator inhibitor type 1 or 2, and with methods of destroying tumor cells using such conjugates.

GENERAL BACKGROUND

Components of the plasminogen activation system. Two types of plasminogen activators, uPA (urokinase plasminogen activator) and tPA (tissue plasminogen activator) are known to convert nonactive plasminogen to plasmin. Both types catalyze the specific reaction, converting the plasminogen to plasmin by cleaving a single peptide bond. Both enzymes also form inactive complexes with specific inhibitors: the plasminogen activator inhibitors type 1 and 2 (PAI-1 and PAI-2).

Urokinase plasminogen activator. uPA's major function is in tissue-related proteolysis, and is important in the processes that entail the dissolution of the extracellular matrix and transversion of basement membranes. It is produced by cells and is present in extracellular fluid in the form of an inactive, single chain proenzyme (pro-uPA). Conversion of pro-uPA to active two-chain uPA by catalytic amounts of plasmin is a crucial regulatory step in plasminogen activation. This conversion provides active uPA and enables an autocatalytic acceleration of uPA formation, (Mayer, M., 1990, Biochemical and Biological Aspects of the Plasminogen Activation System, Clin. Biochem, 23:197–211) uPA is over expressed on the surface of cancer cells when compared with their normal noncancerous counterparts or normal physiological levels of this enzyme.

Urokinase plasminogen activator receptor. Binding of uPA to its specific receptor on the cell surface is important for the localization of uPA catalyzed plasminogen activation. Binding of uPA to its specific receptor on the cell surface is rapid, saturable, and with a high affinity of $10^{-1}$ M. The bound enzyme is not internalized or rapidly degraded. Binding of uPA to the receptor does not involve the catalytic site of uPA; it occurs at the EGF domain of uPA and pro-uPA. Therefore, bound uPA retains its enzymatic activity. Single chain pro-uPA binding to the cellular receptors is followed by conversion of the bound enzyme to active, two-chain uPA on the surface of the cells. Receptor bound uPA can still bind PAI-1 or PAI-2 and maintain its susceptibility to inhibition by these inhibitors. The inhibitors trigger a series of events leading to the internalization of the PAI-1/uPA/uPAR complex. The complex would most likely be degraded in the lysosome and the uPA receptor would probably be recycled.

Tissue plasminogen activator. tPA is a 70 kDa glycoprotein which is primarily active in fibrinolysis and thrombolysis. The major function of tPA, which is identical to the uPA function, seems to be limited to intravascular proteolytic activity. Expression of this enzyme in tumors seems to be random and not related to the malignant state of solid tumors Jankun J., Merrick H. W., Golblat P. J., 1993, Expression and Localization of Elements of the Plasminogen Cancers, J. Cellular Biochem. 553:135–144.

Plasminogen. Plasminogen, the physiological substrate for PAS (plasminogen activators) is a 90 kDa, single chain glycoprotein that is converted to plasmin. The essential step in the activation process is cleavage of a single arginine-valine bond which links the A- and B-chain of plasminogen. When plasminogen is activated to plasmin, it is able to attack a broad spectrum of matrix and basement membrane proteins. Additionally, the plasmin converts pro-collagenase to active collagenase whereby the uPA and plasmin function as essential elements in matrix degradation.

Inhibitors. Emergence of premature and uncontrolled activity of PAs, and activity at inappropriate site(s), is potentially damaging. Inhibition of catalytic activity of PA(s) is, therefore, instrumental in the prevention of aberrant plasminogen activation. It is, therefore, no surprise that potent and specific inhibitors of PAs are present in cells and other extracellular compartments. The major function of these inhibitors is to regulate the catalytic activities, since the balance between enzymes and inhibitors determines net activity. Three inhibitors of uPA activity are known: PAI-1, PAI-2, and protease nexin (Mayer, M., 1990, Biochemical and Biological Aspects of the Plasminogen Activation System, Clin. Biochem, 23:197–211). Two of them are the subject of anticancer therapy: PAI-1 and PAI-2.

Plasminogen activator inhibitor type 1. Plasminogen activator inhibitor type 1 (PAI-1) is a 50 kDa single chain glucoprotein that rapidly and specifically forms equimolar, inactive complexes with two-chain uPA. PAI-1 has significant homology with members of the serine protease inhibitor (serpin) family. Serpins share structural features, a common functional principal, and are important regulators of physiological processes. The PAI-1 forms 1:1 complexes between tPA and uPA inactivating them completely. Although, PAI-1 is synthesized in an active form, it is rapidly converted to an inactive (latent) form.

Molecular basis of the PAI-1 activity. Plasminogen activator inhibitor 1 (PAI-1) is a specific and fast acting inhibitor of both the tissue plasminogen activator (tPA) and urokinase plasminogen activator (uPA). Like other serpins, PAI-1 has a reactive center located on a highly strained exposed loop near the C-terminus of the molecule. The "reactive center" of PAI-1 contains the "bait" peptide bond between residues R(346) and M(347) (M-methionine, R-arginine), i.e., the P1-P1' residues. This bond mimics the R(560)-V(561) (V-valine) bond of plasminogen, which is the bond cleaved by the plasminogen activators during the activation of plasminogen to plasmin. On the basis of the mechanism of the action of other serpins, it has been postulated that PAI-1 binds specifically to the plasminogen activators like substrates (Seetharm R., Dwivedi A. M., Duke J. L., Hayman A. C., Walton H. L. Huckins N. R., Kamerkar S. M., Coarman J. L., Woodeshick R. W., Wilk R. R., Reilly T. M., 1992, Purification and Characterization of Action and Latent Forms of Recombinant Plasminogen Activator Inhibitor 1 Produced in *Escherichia coli*, Biochemistry, 31:9877–9882).

The PAI-1 can exist in two different forms, in the "active" form or in the "latent" form. The active form of the protein is spontaneously converted into the latent form, which can be partially reactivated by treatment with a detergent or with the guanidine hydrochloride. It has been postulated that the latent form of PAI-1 has a greater number of residues from the strained reactive center loop inserted between sheets 3 and 5 in the deducted structure of PAI-1, leading to a collapse of the strained loop and loss of inhibitory activity. The recently solved crystal structure of a latent form of rPAI-1 (recombinant PAI-1) shows that this postulate is essentially true. Latent PAI-1 is inactive presumably because part of its reactive center loop is inaccessible or does not have conformation to bind to its cognate proteases. The residues expected to interact with protease 1, A(357)-Q(362) (A-alanine, Q-glutamine), all reside in the extended loop on the surface of the molecule.

Stabilization of PAI-1 activity. Active PAI-1 can be stored at −70° C. for months with minimal loss in its activity and negligible conversion to the latent form. However, it will be appreciated that PAI-1 loses about 50% of its activity after 2 days at 25° C. or after 2 hours at 37° C. due to conversion of PAI-1 to the latent form (significant conversion of PAI-1 to the latent form also occurs at 4° C. This conversion represents a major challenge in the process to purify, conjugate and store large quantities of active PAI-1 or its conjugates. The latent form of PAI-1 can be reactivated by employing the denaturating agents (6 M guanidium chloride, 1% sodium dodecyl sulfate and others), or more conveniently through heat treatment. Under these conditions the PAI-1 undergoes complete unfolding and can be refolded to its active form after removing the denaturating agents, yielding near 100% of its original activity. Unfortunately, the PAI-1 spontaneously reverses to its latent form again, as quickly as described above.

Plasminogen activator inhibitor type 2. Plasminogen activator inhibitor type 2 (PAI-2) is a 46 kDa serine protease inhibitor with the same function as PAI-1, however with higher affinity for uPA than to tPA. The physiological function of PAI-2 is not clear at this moment, however since it has been found in plasma during pregnancy it has been postulated that PAI-2 functions as a regulator of homeostasis during pregnancy.

Internalization of uPA/uPAR complex by PAI-1 or PAI-2. uPA forms stable complexes with its receptor. Binding of uPA to its receptor is saturable and with high affinity. The uPA/uPAR complex is not internalized or rapidly degraded. The PAI, type 1 or 2, upon binding to the uPA/uPAR complex, initiates a series of events forcing internalization of a formed complex into the cell. Internalization is performed via endocytosis, uPA and PAI are probably degraded, while the receptor is probably recycled.

However, as reported in Danø et al., WO 90/12091 PCT International Application, other elements are needed to internalize the PAI/uPA/uPAR complex. PAI-1 (or PAI-2) bound to uPA arrested to its receptor is approached by a low density lipoprotein-related protein (LRP). After binding to LRP, the tetrameric complex is endocytosed through coated pits. The receptor-ligand-receptor complex dissociates in the acidic environment of the lysosome upon which the ligand (uPA-PAI(s)) is targeted for lysosomal degradation. LRP and the uPA receptors return to the cell surface in a recycling vesicle.

Targeted anticancer therapy. The most important consideration in the selection of antigens used as a target in anticancer therapy is the selection of the cancer specific antigen common for most of the cancers. The most notable property of cancer is its ability to invade and metastasize. The invasive properties of a particular tumor depend on the production of degenerative enzymes such as metalloproteinases, cys and ser proteinases are able to degrade the extracellular matrix. Biochemical markers of malignant tumor cells should be found among the proteolytic enzymes. Indeed, highly metastatic cells synthesize various classes of degenerative enzymes and release them at higher concentrations or activities than their normal counterparts. (Jankun J., Maher V. M., McCormick J. J., 1991, Malignant Transformation of Human Fibroblasts Correlates with Increased Activity of Receptor-bound Plasminogen Activator, Cancer Res. 51:1221–1226; Jankun J. Merrick H. W., Goldblat P. J., 1993, Expression and Localization of Elements of the Plasminogen Activation System in Benign Disease and Breast Cancers, J. Cellular Biochem. 53:135–144). In a number of different tumor models, as well as in tissues derived from human malignancies, a direct correlation has been found between levels of urokinase plasminogen activator activity and/or concentration and the metastatic potential of cancer cells (Jankun et al., 1991, supra.).

The uPA can be secreted to intracellular spaces or bound to the uPA receptor on the surface of the cancer cells. Very often the malignant state of the cancer cells is associated with an increase in the number of receptor bound uPA when compared with the number of uPA molecules bound to the surface of its normal counterparts (Jankun et al. 1991, supra.; Jankun J., 1992, Antitumor Activity of the Type 1 Plasminogen Activator Inhibitor and Cytotoxic Conjugate in Vitro, Cancer Research, 52:5829–5832; Jankun et al., 1993, supra).

The targeted anticancer therapy concept is based on the idea that the localization ability of an antibody is utilized to deliver a therapeutic compound to the tumor. Thus, this compound has to be attached to the antibody, creating an immunoconjugate, in a way that it can be delivered to the tumor without being removed from the antibody before reaching its target. To achieve these goals coupling chemistry, antibody and drug modification techniques, and testing of the resulting conjugates for purity, activity, and specificity have to be investigated and optimized. It is evident now that not only the binding to the antigen, but also the pharmacokinetics behavior of the antibody, can be significantly altered by the coupling process. Since a tumor-specific antibody is usually selected for its particular localization ability, every modification of this protein bears the risk of reducing the target accumulation of the immunoconjugate or even leading to accumulation in nontarget tissues.

There are a number of disadvantages in the use of antibodies as targeting agents. Firstly, the internalization of antibody conjugates into the cell is highly variable, depending on the antibody and the cell. Secondly, the antibody may become itself be antigenic and stimulate an immune response in the patient. Thirdly, the antibody may be cleared from circulation by binding its $F_c$ fragment to the $F_c$ receptor in the liver. Finally, the high molecular weight of the antibodies reduces their ability to penetrate into tumors.

Another approach is to attach the drug or toxin to different growth factors. The growth factors (EGF epidermal growth factor, FGF-basic fibroblast growth factor and others) are usually small molecules that bind to their specific receptors on the surface of normal cells and on cancer cells. Upon binding, the growth factor and receptor are internalized into the cell and the cell receives a very strong signal to proliferate. Many cancers and cancer cells express growth factor receptors on the surface; that makes them an attractive target for anticancer therapy. EGF conjugated with daunomycin was used to reduce the growth of cancer cells in vivo and in vitro (Myers, U.S. Pat. No. 5,087,616). Recently, it has been reported that saporin conjugated with FGF was used in destroying cancer cells in vitro.

Pastan, U.S. Pat. No. 4,545,985, suggested the conjugation of Pseudomonas exotoxin (PE) to different peptides and proteins that react with specific receptors on cells, including sarcoma growth factors, melanocyte stimulating hormone, somatastatin, insulin, transferrin, and low density lipoprotein. Pastan constructed a conjugate of Pseudomonas exotoxin and a peptide hormone isolated from mice epidermal growth factor, by introducing thiol groups in each and then linking the two using a disulfide exchange reaction. The conjugate was toxic to KB tumor cells, but a nude mouse injected with the conjugate died of liver failure. The coupling destroyed the toxin's ability to bind to its own receptor, so toxicity was mediated by receptors of the liver cells.

These methods of treatment are a step forward in targeted anticancer therapy, especially if compared with antibody driven therapy. However, these methods require that all of the cancer will be killed by the growth factor/drug or toxin conjugate. Otherwise, growth factors will stimulate cancer cells to proliferate very rapidly. Instead of tumor growth inhibition, rapid tumor growth occurs.

Another approach to targeted anticancer therapy is the attachment of drugs or toxins to ligands that would secure tumor localization and internalization of such complexes. Danø et al., WO 90/12091 PCT International Application, proposes the possibility of conjugating PAI-1 or PAI-2 with a variety of toxins or drugs to localize and to internalize therapeutically desired medicaments into cancer cells. However, their suggestion is highly speculative (as stated by the authors) and this PCT application does not demonstrate that the binding of conjugated PA(s) to uPA/uPAR is possible, nor that internalization of conjugated PA(s)/uPA/uPAR complexes would be initiated. In that PCT application, Danø et al. neither proves, demonstrates or discusses whether conjugation will involve, alter or block LRP and uPA binding sites which are essential for the orchestrated action of LRP and uPA/uPAR proteins to internalize medicament conjugated PAI(s). Additionally, the authors of this PCT application did not investigate nor do they ever discuss the profound effect of the conversion of PAI to its latent form on the efficacy of the cancer treatment. The preservation of the PAI activity as well as the availability of fully active LRP and uPA sites after conjugation are major challenges in the development of useful PAI driven anticancer therapy. No attempts were made by Danø (WO 90/12091 PCT International Application) to investigate cancer cells killing by PAI(s) medicament conjugates.

OBJECTS OF THE INVENTION

It is an object of the present invention to provide a method of delivering a medicament or cytotoxic compound to the cancer cell and thereafter internalizing the compound into the cancer cell using the pathway of plasminogen activator inhibitor material such as the activated plasminogen activator inhibitor PAI-1 or PAI-2 conjugated with medicament, in such a way that the conjugated medicament will not block the active binding site of PAI or LRP, and prevent conversion of PA into its latent, inactive form to thereby retard or slow cancer growth.

It is an object of the present invention to provide a method of delivery to a cancer cell and entering into the cancer cell a medicament by pathway of plasminogen activator inhibitor material such as activated PAI-1 or PAI-2 that is reactive with uPA and presumably with LRP (to initiate internalization of PAI(s)/medicament complex) that is on the outer surface of the cancer cells.

It is an object of the present invention to provide a method of delivering to a cancer cell and entering into the cancer cell a cytotoxic compound by a pathway of a plasminogen activator material that is reactive with urokinase plasminogen activator (uPA), the cancer cell surface containing a uPA bound to the surface by uPA receptor, the method comprising the steps of:

A. coupling the cytotoxic compound to the plasminogen activator material that is PAI-1 or PAI-2 with a carrier or preserving agent that is equivalent to nanosperes of colloidal gold having a particle size of 1–150 nm to preserve the biological properties of PAI-1 or PAI-2;

B. delivering the reaction product of Step A to the outer surface of the cancer cell and locating the cancer cell thereby to form a reaction product /uPA/uPAR complex; and C. entering the complex into the cell to degrade the complex and deliver the cytotoxic compound inside the cell to reduce the cancer growth.

In the above process PAI-1 and PAI-2 have their biological properties maintained and preserved by preserving agents such as saporin that are equivalent to colloidal gold, the gold preferably having a particle size of 5 to 15 nm and more preferably 12 nm.

These and other objects will be apparent from the specification that follows and the appended claims.

SUMMARY OF THE INVENTION

In the parent application Ser. Nos. 07/889,783 and 08/059,813 (incorporated herein by reference)-cancer growth was retarded using PAI-1 or PAI-2, that was preserved by using nanoparticles of gold in water as set forth in actual laboratory examples of form the colloidal gold/cytotoxic compound/PAI-1 or PAI-2 reaction product.

The present invention provides a method of delivering to a cancer cell and entering the cancer cell a cytotoxic compound by a pathway of plasminogen activator material that is reactive with urokinase plasminogen activator (uPA), the cancer cell surface containing a uPA bound to the surface by uPA receptor, the method comprising the steps of:

A. coupling the cytotoxic compound to the plasminogen activator material that is PAI-1 or PAI-2 with a carrier that is equivalent to nanosperes of colloidal gold having a particle size of 1–150 nm to preserve the biological properties of PAI-1 or PAI-2;

B. delivering the reaction product of Step A to the outer surface of the cancer cell and locating the cancer cell thereby to form a reaction product /uPA/uPAR complex; and C. entering the complex into the cell to degrade the complex and deliver the cytotoxic compound inside the cell to reduce the cancer growth. The step A of coupling the cytotoxic compound to PAI-1 or PAI-2 with a preserving material carrier is performed at a temperature of about 4° C. to 40° C. for a time of about 1 second to 78 hours.

The present invention also provides a method of delivering to a cancer cell and entering into the cancer cell a cytotoxic compound by a pathway of plasminogen activator material that is reactive with urokinase plasminogen activator (uPA), the cancer cell surface containing a uPA bound to the surface by uPA receptor, the method comprising the steps of:

A. coupling the cytotoxic compound to the plasminogen activator material that is PAI-1 or PAI-2 with a carrier that is equivalent to nanospheres of colloidal gold having a particle size of 1–150 nm to preserve the biological properties of PAI-1 or PAI-2;

B. delivering the reaction product of step A to the outer surface of the cancer cell and locating the cancer cell thereby to form a reaction product /uPA/uPAR complex; and C. entering the complex into the cell to degrade the complex and deliver the cytotoxic compound inside the cell to reduce the cancer growth.

The present invention provides a method of delivering to a cancer cell and entering into the cancer cell a medicament, through the pathway of plasminogen activator, material that is reactive with the urokinase plasminogen activator (uPA), that is located on the cancer cell surface, and bound to the cancer cell surface by uPA receptor (uPAR), the method comprising the steps of:

A. coupling the medicament to the plasminogen activator material that is PAI-1 or PAI-2 to form a reaction product in a such way that the medicament does not interfere with active sites responsible for binding to uPA or LRP proteins responsible for internalization of plasminogen activator material/conjugated medicament, and using saporin or another PAI-1 or PAI-2 preserving agent whereby the conjugated medicament prevents conversion of the plasminogen activator inhibitor material (PAI-1 or PAI-2) into its latent inactive form.

B. delivering the reaction product of step A to the outer surface of the cancer cell thereby to form the reaction product/uPA/uPAR complex; and C. entering the complex into the cancer cell to degrade the complex and deliver a medicament inside the cell to reduce cancer growth.

A preferred method of delivering the medicament is by crosslinking the medicament to PAI-1, PAI-2, PAI-1 derivative or PAI-2 derivative with a preserving agent such as saporin to form a reaction product.

Preferred medicaments may be typically toxins e.g. saporin, A-chain ricin, A-chain cholera toxin, cobra venom, or an anticancer agent such as an alkylating agent, e.g. cisplatin, chlorambucil, melphalan, or an antimetabolite agent such as methotrexate, fluracil or an antibiotic such as doxorubicin or bleomycin.

The reaction product of the coupling step is made generally at a temperature of about 4° C. to 60° C. and preferably about 8° C. to 40° C. for a time of, generally, about 1 hour to 144 hours and preferably about 12 hours to 72 hours.

Using the plasminogen activator inhibitor material pathway, the PAI/medicament conjugation product is not only delivered to the cancer cell but also couples with the uPA/uPAR and LRP on the cell surface whereupon the resultant reaction product/uPA/uPAR/LRP complex is efficiently internalized within the cell while the complex is degraded to deliver medicament within the cell to stop, slow down or retard cancer growth.

The present invention includes the following:

1. Finding and providing the cancer markers or cancer associated antigens (cell surface associated) present in common cancers.

2. Selecting a cancer marker or cancer associated antigens and a high affinity binding ligand, which upon binding to cancer associated marker will be internalized into the cancer cells.

3. Providing a suitable crosslinker that is stable in circulation but clearable inside the cancer cells to potentiate effect of medicament on the cancer cells.

4. Selecting a suitable medicament to kill the cancer cells upon internalization of the tumor localizing/medicament complex.

5. Selecting a method of crosslinking the cancer localizing molecule and medicament that would prevent the conversion of the cancer localizing factor to its latent, inactive form.

Cancer markers or cancer associated antigens. The malignant potential of solid tumors is related to their proliferation rate as well as to their capacity for invasion and metastasis. The potential of cancer cells for tissue invasion and hematogenous spread is related to their capacity to dissolve the structures in their vicinity. Since the structure of the penetrated tissues consists mainly of proteins, e.g., fibronectin, fibrin, protoglycans, or collagen, the primary substances used by a tumor cell for invasion and metastasis are proteases. Tissues of primary cancer and/or metastases of the breast, ovary, cervix uteri, bladder, prostate, liver, lung, and gastrointestinal tract have been reported to contain high levels of cathepsins, collagenase IV or urokinase plasminogen activator (uPA) when compared with benign tumors or normal tissues (Jankun et al., 1991 supra., Jankun et al., 1993, supra.). Elevated levels of Cathepsin D and uPA are of clinical significance. It has been reported that increased concentration of those proteases in breast tumor tissues may predict a high risk of metastasis and shorten overall survival when compared to patients with smaller amounts of those factors. Elevated levels of uPAR have been reported in breast cancer also, and overexpression of uPA is often accompanied by the coexpression of uPA as it is explained in Example 1 (Jankun et al., 1993). These facts make uPA and uPAR proteins very attractive targets in anticancer therapy.

Cancer markers or cancer associated antigens that can internalize a medicament upon binding uPA and/or uPAR could be targeted using a ligand (amino terminal fragment of uPA to target receptor) or polyclonal and monoclonal antibodies. However, these tumor localizing factors do not secure internalization of a conjugated medicament. Additionally, monoclonal antibodies, murine in origin, could, as a consequence produce negative side effects ranging from allergic reaction to anaphylactic shock.

Another way of delivering the medicament to cancer cells is to conjugate it with PAI-1. PAI-1 binds to uPA/uPAR overexpressed on the surface of cancer cells with high affinity ($10^{-13}$ M). The binding is strong and only then, after binding to LRP, PAI-1 triggers internalization of the medicament/PAI-1/uPA/uPAR/LRP complex. The complex is degraded, receptors are probably recycled, and products of protein degradation and medicament are released to the cytosol. The concept of tumor targeting with the plasminogen activator inhibitor as a ligand is based on the overexpression of urokinase plasminogen activator and its receptor on the surface of cancer cells when compared with normal tissue. The PAI-1 is a cancer cell localizing and internalizing molecule in a PAI-1 based medicament. As a protein of human origin, it is not immunogenic and, therefore, is superior to murine antibodies proposed for targeted cancer therapy.

Additionally, new facts have been reported, making PAI-1 cancer therapy even more attractive. A direct correlation has been found between the expression of uPA and uPAR and the formation of capillary sprouts. This mechanism for new blood vessel formation (angiogenesis) is one of the essential elements of tumor formation. Destruction of capillary sprouts initially causes blood leakage in the vicinity of a tumor mass and increases the amount of medicament diffusing into the tumor. Later, the PAI-1 based anticancer treatment could prevent the formation of new vessels and limit or prevent new growth by restricting the delivery of nutrients to the tumor mass. These findings broaden the potential use of this conjugate in proposed anticancer therapy.

Unfortunately, PAI-1 is not a stable protein, it spontaneously converts itself into a latent, inactive form. The latent form of PAI-1 does not possess the ability to bind to uPA and therefore is useless in anticancer therapy. Suitable ribosome-inactivating proteins (RIP) preserving agent compounds are byrodin, momorochin, and momordin. In a preferred embodiment, the ribosome-inactivating proteins (RIP) preserving agent compounds are saporin and gelonin. We found that the modification of PAI-1 molecule with the heterobifunctional crosslinker SMPT [4-succinimidyloxycarbonyl-α-methyl-α-(2-pyridyldithio)toluene] and later conjugation of modified PAI-1 with saporin prevents the conversion of an active form of PAI-1 into its inactive form. We hypothesize that saporin conjugated by SMPT with PAI-1 is creating a space hinderance in the proximity of the strained loop of PAI-1. This space hinderance prevents the strained loop, that is responsible for PAI-1 activity, from retracting into the PAI-1 molecule. As a consequence the PAI-1 molecule is "frozen" in its active state as therapeutically desired.

Heterobifunctional crosslinker of saporin and PAI. Crosslinking or conjugating reagents are chemical compounds used to couple covalently two or more molecules by reactive functional groups in their structures. Crosslinkers (preserving agents) contain at least two reactive groups, usually at opposite ends of the molecule, which can be homobifunctional or heterobifunctional. Homobifunctional crosslinkers are less effective than other crosslinkers and have a tendency to produce very high molecular polymers of conjugated proteins. Heterobifunctional crosslinkers involve two steps for conjugation and are often used to prevent undesirable self conjugation which occurs with the homobifunctional reagents. The type of crosslinker used to make the conjugate can affect the ability of the conjugate to kill the cell. Thiol clearable conjugates have been shown to be more cytotoxic to tumor cells than nonclearable conjugates. SMPT [4-succinimidyloxycarbonyl-α-methyl-α-(2-pyridyldithio)-toluene], a thiol reactive and clearable crosslinker, contains a benzene ring and a methyl group adjacent to a carbon next to the disulfide bond.

Another crosslinker is a maleimide derivative of 2-methylmaleic anhydride that has been used to generate an antibody-gelonin conjugate with acid liable bond. The reaction of the amino group of gelonin with 2-methylmaleic anhydride gives a substituted maleyl derivative whose carboxamide bond is susceptible to hydrolysis under mildly acidic conditions pH of 4 to 5 (Wong S. S., Chemistry or Protein Conjugation and Cross-linking, CRC Press, Boca Raton, Ann Arbor, Boston, London, 1993).

Another compound that generates an acid clearable amide linkage on reaction is 4-(iodoacetyloamino)-3,4,5,6-tetrahydrophthalic anhydride. It has been used to conjugate interlukin 2 to gelonin. Although, the reaction reduces the activity of the antibody significantly, the toxin is released in native and fully active form by mild acid treatment (Wong, 1993, supra.).

Medicament. PAI-1 modified by SMPT could be conjugated with virtually any anticancer drug or toxin if these substances bear a functional group (—SH) that could react with SMPT. If the substance lacks a suitable functional group, it could be modified by generally known chemical methods to introduce an —SH group. In this stage of investigation we chose to use saporin as an anticancer toxin. Saporin is a ribosome inactivating protein (RIP) type 1. A type 1 RIPs contain one chain and enter cells with difficulty, as they are devoid of the binding B-chain that type 2 RIPs contain. As a consequence the saporin is much safer to work with, but is equally potent as the type 2 RIP if delivered into the cancer or normal cells. The entry of type 1 RIP or A-chain of type 2 RIP into the cell inactivates the ribosomes; thus the protein synthesis is arrested and cell death occurs (Barbieri L., Battelli M. G., Stripe F., 1990, Blood Clearance and Organ Distribution and Tissue Concentration of Native, Homopolimerized and IgG-conjugated Ribosome Inactivating Proteins, Xenobiotica, 20:1331–1341; Thrope et al., 1987, supra.).

Crosslinking PAI-1 with medicament prevents conversion of the active form of PAI-1 to its latent form. Unexpectedly, under specific conditions of conjugating (concentration of PAI-1 1.45 μM, concentration of SMPT below 2 μM, molecular ratio of PAI-1 to saporin 1:4, denaturating conditions of conjugation) PAI-1 with saporin exemplified in Example 2, the conjugated medicament prevents or significantly slows down the conversion of an active form of PAI-1 into its inactive, latent form. A very high speed of conversion of PAI-1 into its inactive form was a major challenge during synthesis, purification and storage of active PAI-1. Additionally, a fast conversion, if not prevented, makes it impossible to use PAI in anticancer therapy. The time needed to synthesize, purify, and reach the tumor site was much longer than the life time of the active form of PAI-1. We have synthesized active and inactive forms of PAI-1/saporin conjugates. As shown in Example 3, tumor cell killing was observed when the active form was used, while no cell killing was observed when the inactive form of the PAI-1/saporin conjugate was applied.

The RIP compounds have number average molecular weight of about 20,000 to 40,000 daltons and preferably about 28,000 to 32,000 daltons.

EXAMPLE 1

Materials and methods—actual laboratory tests.

The breast tissues were from resected specimens retained in the pathology department, archives at Medical College of Ohio from 1991 to 1992. Representative tissue blocks were selected and were fixed in 10% phosphate-buffered formaldehyde (pH 7.4) and embedded in paraffin wax. Tissue sections, 5 μm thick were stained with hematoxylin and eosin for routine histological evaluation. Slides were reviewed by a surgical pathologist and were classified as: 3-normal breast, 3-fibroma, 2-infiltrating adenocarcinoma, 1-ductal carcinoma in-situ, 2-ductal carcinoma, 3-infiltrating ductal carcinoma.

Adjacent serial sections were mounted on poly-L-lysine coated glass slides, deparaffinized in xylene followed by chloroform, and used for immunohistology, using a peroxidase/diaminobenzidine procedure. Briefly, the tumor sections were blocked for endogenous peroxidase activity in 0.3% $H_2O_2$ methanol for 5 minutes. Next, sections were rehydrated in descending ethanol washes, washed in phosphate buffered saline, pH 7.4, and blocked in blocking solution for 30 minutes (blocking solution contains carrier solution—96 ml of PBS, 1 g of crystalline bovine serum albumin, 3 ml of 10% TWEEN™ and 20% of normal goat serum). Next, sections were incubated with primary antibodies in carrier solution for 60 minutes at 37° C. Affinity purified murine monoclonal antibody against uPA, class $IgG_1$, 8 μg/ml was used. The antibody #3689 is directed against an epitope within the β-chain of uPA and recognizes pro-uPA, high molecular weight uPA (HMWuPA), and low molecular weight uPA (LMW uPA). This antibody recognizes free and complexed uPA, and does not crossreact with tPA. Additionally in some experiments two different monoclonal antibodies against uPA were used: #377, and #394. To insure authenticity of uPA binding the monoclonal antibodies #3689 and #377 were preincubated with uPA (24 µg/ml) and incubated with three samples of malignant breast tissue. No staining was observed. Murine antibody #3936, class IgG$_{2a}$, 40 µg/ml was used to detect uPAR. The antibody recognizes non-complexed and complexed uPAR, however, saturation of the receptor with HMW uPA and pro-uPA might result in drastic reduction (ca. 50%) of binding monoclonal antibody #3936 to the receptor. All primary antibodies were supplied by American Diagnostica Inc., Greenwich, Conn. The reactivity of these antibodies in immunohistochemical procedures has been verified independently. Subsequently the sections were incubated with goat anti-mouse antibody (product number 31432X from PIERCE, Rockford, Ill.), 40µg/ml for 30 minutes at 37° C. Antigen staining was identified by the brown reaction products of peroxidase with diaminobenzidine. Sections from normal kidney, in which tubule cells are positive for uPA and uPAR, served as positive controls. Negative controls consisted of incubation with non-immune mouse serum and incubation with secondary antibody only, with the remaining steps unchanged. Second negative control samples include preincubation of malignant tissue samples with antibodies preadsorbed with antigen (uPA), with remanding steps unchanged. The preincubation abolished staining of malignant breast cancers. Immunohistochemical staining of antigens was evaluated blindly for intensity and semi-quantitative evaluation of the percentage of positive (neoplastic) epithelial cells as follows: 1=no positive cells; 2=few cells with weak positivity; 3=few cells with distinct positivity; 4=weak positivity of all cells; 5=weak to distinct positivity in most cells (with focal negative areas); 6=weak to distinct positivity in all cells; 7=distinct positivity in all cells. Statistical analysis of immunohistochemical values and clinical data were performed using Student's t test and the $\chi$ test of the independence of categorical variables. Differences were considered significant when $P \leq 0.05$.

Results of actual laboratory tests.

Immunohistological uPA staining. To insure the authenticity of staining patterns as positive controls we used the following antibodies: #377, #394, #3689 for at least two different samples of normal breast, normal kidney, benign breast and malignant tissues. All of them showed the same staining pattern, but with different intensity. The antibody #3689 showed the strongest intensity of staining and was chosen for future study. Preadsorbtion of antibodies #3689 and #377 with uPA, abolished staining of malignant breast tissues, and served as negative control. Distinct differences were observed between the immunohistological uPA staining intensities of benign and malignant tumors. The benign tumors, as well as normal breast tissue, showed a range of weak positivity to distinct positivity in the ductal epithelium, most prominent on the apical surface of the cell. The malignant breast tumors showed a wide spectrum of staining intensities. In general, we found diffuse cytoplasmic staining, sometime localized in the nucleus, and in some cases strong cell membrane staining for uPA. No nuclear staining was observed in benign tumors. Patchy and diffuse staining of adipose and/or fibrous connective tissues was observed when malignant tumors stained very intensely for uPA. Some distinct staining of scattered macrophages occasionally was detected also. For benign tumors the mean uPA score was 2.5±1.0 (SD), while for malignant tumors the mean uPA score was 6.1±0.8. The immunohistochemical staining intensity of uPA was found to differ significantly in benign and malignant tumors (t=14.365, P=0.0005).

Immunohistochemical uPAR staining. There is no commercially available antibody directed against uPAR, except #3936. Sections of normal kidney served as positive controls. The tubule cells of kidney are known to contain high amounts of uPAR. Intensive staining was observed within the tubule cells, when the other surrounding cells remained unstained. No staining was observed in 33% of benign tumors or normal breast, and weak to distinct positivity was detected in the rest for uPA receptor. When benign tumors stain for the receptor, the highest intensity was observed on the duct epithelium, and much weaker intensity was seen within rest of the lobules. In contrast, malignant tumors showed a variety of uPAR intensity, mostly distinct or strong intensity of staining within the tumors. Distinct staining was observed on the cell membrane and occasionally in the nucleus of cancer cells. The phenomenon of nuclear staining for uPAR was not observed in the benign tumors. Virtually no positivity was detected in extracellular spaces. The positivity for uPAR of benign tumors was weak with the immunohistochemical score rather low; mean 2.2±1.3, while the malignant tumors scored high; mean 5.3±1.3. Those two score populations were statistically different (t=3.520, P=0.005).

Discussion

These studies were undertaken to test the hypothesis that uPA and uPAR activity would be present in high levels in malignant human breast tumors, suggesting that the plasminogen activator system functions in the tumor invasion and/or metastatic processes. The results support the hypothesis that uPA, uPAR, are overexpressed as determined by immunohistology using monoclonal antibodies #3689, #3936. Neoplastic tissues of breast were found to exhibit elevated levels of uPA, uPAR. Overexpression of uPA, uPAR have been found to correlate well with the malignant state of tumor cells. High exhibition of tPA found in cancer seems to be random and not related to the malignant or benign state, since benign and malignant tumors show overexpression of tPA with similar frequency. Human carcinomas originating from colon, stomach, uterus, ovary, breast, and prostate have been found to be positive for uPA by histological evaluation. These observations, as well as an in vitro study (Jankun et al., 1991, supra.), illustrate that malignant transformation of cells is associated with an increased intracellular content of uPA, an antigen which is only sporadically observed in their normal tissue counterparts. With respect to the subcellular localization of uPA, we found a diffuse cytoplasmic staining in the cytoplasm (benign and malignant tumors), and/or cell membrane staining of uPA that is in accordance with most other studies. Presence of the uPA in the cytoplasm and on the cell membrane correlates well with the theory of uPA localization and activation. Localization of uPA in the nucleus was not reported; however, appearance of anti-uPA staining is obvious from some photographs of other investigators. In contrast to one report (Danø et al., 1992) we do not find any strongly positive normal cells or macrophages in tissue adjacent to the tumor. The lack of staining for uPA in this study can be associated with the type of antibody used (e.g. not able to detect uPA that is receptor-bound and/or complexed with PAI-1) and the lack of straining was reported by others. Light, occasional staining of normal tissue for uPA could be associated with uPA secreted by cancer cells, or can be positive in granulocytes, natural-killer cells, fibroblasts or macrophage-like cells.

While systematic overexpression of uPA in breast cancer has been abundantly documented, histopathological localization of uPAR in breast cancer has not been studied widely. In fact most studies were conducted on tumor extracts or cell lines. Similarly, as in the case of uPA, uPAR is overexpressed by cancer cells. Benign tumors do not express uPAR at all, or express it in very small amounts. Overexpression of uPAR in a breast cancer cell line has already been documented, but there has been no systematic histopathological study of its localization. The necessary presence of the cell surface uPA localizing molecule, uPAR, in cancer invasion and metastasis was anticipated and some evidence already exists (Jankun et al., 1991, supra.). It appears that one of the functions of uPAR, in addition to simply providing a mechanism for confining uPA to the cell surface, is to localize uPA to discrete areas of the cell surface. In this way uPAR would direct proteolytic activity against normal tissue and would spare the cancer cells expressing it. We analyzed all our samples to find evidence of such localization. However, only in some cases, when uPAR is present in moderate amounts, can such localization be detected. In cases of overexpression of this antigen, it was not only localized on the cell surface of the tumor's leading edge, but present in all cancer cells and sometimes in the nucleus of the cancer cell. We were not able to confirm the fact of exhibition of uPAR in the nucleus of cancer cells.

When the tumors exhibit high amounts of uPA, they also exhibit a high amount of uPAR in 50% of the cases. When uPA is expressed in low amount, the uPAR is low in 28.6% of the cases. This of the cases statistically significant consensus, 78.6% of analyzed cancer cases in a case of cases uPA/uPAR, suggests that activity of uPA and uPAR, may be the result of a unique mechanism of control, activated in the last steps or step of carcinogenesis. This regulatory mechanism or pathway is not known yet, but is in agreement with our results and has been postulated by others (Jankun et al., 1991, supra.).

EXAMPLE 2

Materials and methods—actual laboratory tests

Conjugation of the saporin and plasminogen activator inhibitor PAI-1. An immunotoxin has been produced by crosslinking saporin and the plasminogen activator inhibitor using the heterobifunctional crosslinker SMPT [4-succinimidyloxycarbonyl-α-methyl-α-(2-pyridyldithio) toluene]. This conjugate incorporates a disulfate bond adjacent to the benzene ring and methyl group. Such a configuration imparts plasma stability (a half life over 24 h in comparison to less than 12 h for SPDP (N-Succinimidyl 3-(2-pyridyldithio) propionate) and an acid-labile disulfide bond which liberates saporin once it is internalized into the acidic environment of lysosomes. This action potentiates (up to 1000 times) the cytotoxic action of ribosome inactivating saporin.

Heterobifunctional crosslinking of saporin and PAI-1 was performed, with some modification, as described by Blakely. Blakely D., Watson G., Knowels P. Thrope P., 1987, Effect of Chemical Deglycosylation of Ricin A-chain on the in vivo Fate and Cytotoxic Activity of an Immunotoxin Composed of Ricin A-chain and anti-Thy 1.1 Antibody, Cancer Research, 47:947). Briefly, a PAI-1/SMPT derivative was synthesized by adding the acetonitrile solution of SMPT to the phosphate buffered saline (PBS), 1% SDS (sodium dodecyl sulfate), pH 7.4, solution of PAI-1. The reaction was performed for 2 hours at room temperature. The crosslinker was used in different concentrations that vary from 0.1 mM to 10 mM. The conjugate was used in 0.1–4 fold excess of PAI-1. The reaction mixture was purified by gel filtration (Speedy Desalting Columns, Pierce, No.43243 X) to remove an excess of crosslinker.

It is not clear whether saporin contains thiols or reducible disulfide and thus requires introduction of thiols onto the surface of the toxin. For this purpose Traut's reagent (2-Iminothiolane) was used. The saporin in the TRIS-HCl buffer, pH 8.0, was incubated with Traut's reagent in a 5 X molar excess at room temperature for 45 minutes. Separation of the iminothiolated protein from the excess of 2-Iminothiolane was performed on the desalting column.

The second part of the reaction for the production of the immunotoxin via sulfhydryl group to the SMPT modified PAI-1 was done in PBS, 1 mM EDTA, 1% SDS buffer, pH 7.4. This reaction is considerably slower and was carried out for 72 hours. The efficiency of the second reaction was quantified by measuring the amount of pyridine-2-thione released as a by-product (the extension coefficient of pyridine-2-thione is $8.08\pm0.3\times10^3$ $M^{-1}cm^{-1}$ at 343 nm) (Blakely et al., 1987, supra.). The immunotoxin was separated from the by-products by gel filtration, then aliquoted and frozen in liquid nitrogen for future use.

Determination of PAI-1 activity of PAI-1/saporin conjugate. The PAI-1/saporin was incubated with an equimolar amount of uPA (1 μg) in PBS, pH 7.4, for 10 minutes. Next, the solution was incubated with 0.25 mM of SPECTROZYME® UK (American Diagnostica, Inc.) and the absorbance of generated free chromophore was determined spectroscopically at 405 nm. A recombinant PAI-1 was used as a positive control. As a reference and negative control, the non-inactivated uPA was used.

Results (actual laboratory test)

Conversion of active PAI-1 to its latent, inactive form as a function of time. All experiments were preformed at room temperature. A significant loss of activity was observed after 24 h of incubation, that progresses after 48 and 72 h.

Effect of SMPT modification of activity of PAI-1. Heavy modification of PAI-1 by SMPT could have a negative effect on the activity of plasminogen activator inhibitor. To check for this, the PAI-1 was modified using different concentrations of SMPT. We found that modification of PAI-1 using a concentration of SMPT 2 μM and higher reduces the activity of PAI-1 up to 5 times. In all future experiments we used a concentration of SMPT below 2 μM that does not reduce the activity of PAI-1.

Conjugation of the saporin and plasminogen activator inhibitor PAI-1. Saporin is a ribosome inactivating protein (RIP) and it was estimated that a single molecule in the cytoplasm is sufficient to kill the cell (Barbieri et al., 1990, supra.). The $LD_{50}$ is estimated to be 2000 μg/kg of the mouse's body weight (Cavallaro U., del Vecchio A., Lappi A. D., Soria M., 1993, Antitumor Activity of UPA/Saporin Conjugate In Vitro, NATO Advanced Study Institute, Targeting of Drugs: Advances in System Constructs, 24 Jun.–5 Jun., 1993, Cape Sounion Beach, Greece; Barbieri et al., 1990, supra.). Although it has been reported that while saporin is conjugated with antibodies or growth factors, it can be introduced into lisosomes and later into the cytosol. This greatly increases the toxicity of saporin (Barbieri et al., 1990, supra.). For these reasons saporin was chosen as the cytotoxic part of the conjugate.

Initial conjugation of PAI-1 and saporin using a covalent heterobifunctional crosslinker (no SDS was used) has produced a conjugate that possesses very little PAI-1 activity (less than 1-2%). Furthermore, the activation of this conjugate by 1.0% SDS resulted in PAI-1's activity being less than 5%.

To overcome the problem of the lack of PAI-1 activity, all conjugation was preformed under a denaturating condition using a 1.0% solution of SDS. The PAI-1/SAP conjugate synthesized in this way possesses 89% of PAI-1 original activity. To minimize the loss of PAI-1 activity, the time needed to crosslink PAI-1's and saporin was analyzed by monitoring the amount of pyridine-2-thione released as a by-product during conjugation. The maximum amount of pyridine-2-thione was reached after 72 h and future conjugation was performed in the same manner.

Stabilization of PAI-1 activity after conjugation with saporin. Non-conjugated PAI-1 lost most of its activity after 72 h of incubation while the saporin/PAI-1 (1:4) conjugate still possess at least 60% of its original activity.

Discussion

The inhibitors of the serpin family (PAI-1 is a member of this family) have a reactive center located on the exposed loop, referred to as the strained loop, situated near the carboxyl terminus of the molecule. Although the precise mechanism(s) by which the serpins inhibit their target proteases are not well understood, they are known to interact with their target proteases by providing a so called "bait" residue (P1 residue), located within the strained loop. This loop mimics the normal substrate of the target protease. However, other residues in close proximity to the P1 also may play a role in determining inhibitor specificity.

The heterobifunctional crosslinker binds to primary amines of aminoacids; e.g. lysine and the aminoterminal of the protein. The strained loop does not possess lysine and is not located on either end of the protein chain. No binding sites are available for chemical modification by SMPT and no loss of activity is expected from the direct binding of SMPT. However, if PAI-1 was to be heavily modified, it may loose uPA binding activity by creating a space hinderance in close proximity to the PAI-1 active site. This unwanted effect was avoided by modification of PAI-1 by SMPT that was below 2 µM.

An unexpected finding was the protection of PAI-1 activity in the saporin conjugated plasminogen activator inhibitor. This finding could be explained in the following way: The serine protease inhibitors all function by forming tight complexes with their target proteases. The external position of the reactive center loop makes it vulnerable to proteolytic cleavage and serpins are readily inactivated in this way. Cleavage of the reactive center results in profound structural changes, with the peptide loop being inserted into the protein A-sheet to give the stable, inactive relaxed (R) form of the molecule. This change from the native stressed (S) form (often called active form) to relaxed form (R) is a characteristic feature of inhibitory serpins. However, serpins can be inactivated by the insertion of the center loop into a protein without the proteolytic cleavage of the strained loop. This form is called the locked (L) form or often called latent form. PAI-1 and other serpins can be reactivated from the L conformation by exposure to denaturating agents and refolding to a fully active S conformation. Thus, PAI-1 can be protected from conversion into the L conformation by binding to the vitronectin that holds the reactive center loop out of the A-sheet. A similar effect could be achieved by creating a space hinderance of SMPT molecules or SMPT conjugated proteins. It seems that the molecular ratio 1:4 of PAI-1 to SMPT in conjugated proteins prevents the collapse of the reactive center of PAI-1 into the molecule, and does not reduce its activity in at least some conjugates. This effect is therapeutically desired, and makes it possible to synthesize, purify and use saporin/PAI-1 conjugates in anticancer treatment.

EXAMPLE 3

Materials and methods—actual tests

Cells and Cell culture. The sources of cells are as follows: normal fibroblast—KD and fibrosarcoma HT1080 are from American Type Culture Collection, bladder carcinoma derived cells—BL28 were obtained from Dr. Pamela Russell of the Oncology Research Center, University of New South Wales, Randwick, Australia. The cell lines were routinely cultured in αMEM medium containing penicillin (100 units/ml) and streptomycin (100 µg/ml). The medium was supplemented with 10% new-born calf serum (HyClone, Logan, Utah). The cells assayed for PA and cancer cell killing activity were in exponential growth at the time they were tested. The cells assayed for these activities were cultured in a medium without antibiotics 24 h prior to and during assays.

In Vitro Survival Studies. Cells were plated in 96-well microtiter flat-bottomed cell culture plates (approximately 250 cells/well). They were treated in triplicate with different concentrations of PAI-1/SAP immunotoxin for 72 h in an antibiotics-free cell culture medium and maintained at 37° C. in 5% $CO_2$. At the end of the incubation period, the cells were washed, fixed, and stained in 0.1% Crystal Violet solution. Next, the cells were counted under the microscope and normalized to control population.

Assay of Antitumor Activity of PAI-1/SAP In Vivo. SCID mice (T and B cell deficient) weighing 20–25 g, were used (Medical College of Ohio). The animals were housed, 1/sterile cage, with access to sterile rodent chow and sterile water ad libitum. The photoperiod was maintained on a 12 hour light, 12 hour darkness cycle. The experiments were approved by the Animal Care and Use Committee at the University of Toledo.

Cancer cells were injected in the rear flank, $1\times10^6$ HT1080 fibrosarcoma cells. Animals were monitored for evidence of tumor growth. The mice were treated by injections of 200, and 2000 µg of PAI-1/SAP per kg of body weight into the tumors when tumors reached a volume of approximately 1000 $mm^3$.

At the end of the experiment the animals were sacrificed and the tumors were surgically removed, examined, weighed and fixed in formaldehyde. Next, the formaldehyde fixed tumors were paraffin embedded, sectioned, and stained with hematoxylin and eosin then examined under the microscope.

Results

Studies of cancer cell killing In Vitro. To study cell killing three different cell lines were selected: KD—normal fibroblasts (expressing less than 0.2 $I/10^6$ cells/24 h receptor bound uPA), HT1080 fibrosarcoma derived fibroblasts (expressing 22.7 $I/10^6$ cells/24 h receptor bound uPA), and BL28 bladder carcinoma epithelial cells (expressing 37.6 $I/10^6$ cells/24 h receptor bound uPA). In addition to the previously studied KD and HT1080 cells, bladder carcinoma cells BL28 were added as a possible model of bladder cancer. This cancer could be treated locally simplifying the treatment. This cell line was selected as a cell line that overexpressed uPA and uPAR and produced tumors in the athymic mouse.

The cells were treated as described in the materials and methods section and were killed by activated PAI-1/SAP cytotoxin. Very little killing was observed in the case of normal fibroblast expressing little receptor-bound uPA, more in the case of HT1080 expressing a moderate amount of receptor-bound uPA, and the highest rate of killing was observed in the case of BL28 possessing the highest amount of receptor-bound uPA. Moreover, the cell killing was PAI-1/SAP concentration dependent. No cell killing was observed using PAI-1/saporin conjugate that did not possess PAI-1 activity.

Assay of Antitumor Activity of PAI-1/saporin In Vivo. The PAI-1/saporin cytotoxin was injected into the tumor on the seventeenth day, after tumor cell implantation. Drastic differences were observed in the tumor growth of treated and untreated animals. In the case of animals treated with the highest dose, tumor reduction was observed (2 times in volume) while the control tumor increased its volume 5 times in the same time. At day 24, the animals were sacrificed, tumors were surgically removed, analyzed, fixed, and the histopathological morphology was analyzed. The tumor of an untreated animal weighed 421 mg and showed no evidence of necrotic tissue. The tumor of an animal treated with a dose 200 µg/kg weighed 251 mg with some necrotic tissue present. Finally, the tumor of an animal treated with the highest dose weighed 201 mg and contained the highest number of necrotic foci.

What is claimed is:

1. A method of selectively delivering a cytotoxic compound into a cancer cell having on an outer surface thereof active binding sites for a reaction product, the method comprising the steps of:

A. coupling the cytotoxic compound to a plasminogen activator inhibitor selected from the group consisting of PAI-1 and PAI-2 modified with a preserving agent to provide the reaction product, the preserving agent preventing conversion of the plasminogen activator inhibitor to an inactive form thereby preserving the biological properties of the plasminogen activator inhibitor; and B. delivering the reaction product of step A to the outer surface of the cancer cell so as to form a complex with one or more of the outer surface binding sites, wherein the complex enters the cancer cell.

2. The method as defined in claim 1 in which the preserving agent is colloidal gold.

3. The method as defined in claim 1 in which the preserving agent is a crosslinking agent containing at least two reactive groups.

4. The method as defined in claim 3 in which the crosslinking agent is a heterobifunctional crosslinker.

5. The method as defined in claim 3 in which the crosslinking agent is a homobifunctional crosslinker.

6. The method as defined in claim 3 in which the crosslinking agent is selected from the group consisting of 4-succinimidyloxycarbonyl-α-methyl-α-(2-pyridyldithio)-toluene, maleimide derivative of 2-methylmaleic anhydride, and 4-(iodoacetyloamino)-3,4,5,6-tetrahydrophthalic anhydride.

7. The method as defined in claim 3 in which the crosslinking agent is a thiol cleavable crosslinker.

8. The method as defined in claim 1 in which the binding sites include a lipoprotein-related protein, a urokinase plasminogen activator bound to a urokinase plasminogen activator receptor and combinations thereof.

9. The method as defined in claim 1 in which the cytotoxic compound is an anticancer agent having a functional —SH group.

10. The method as defined in claim 1 in which the cytotoxic compound is selected from the group consisting of saporin, A-chain ricin, A-chain cholera toxin, cobra venom, an alkylating agent, an antibiotic and an antimetabolite.

11. The method as defined in claim 1 in which the cytotoxic compound is selected from the group consisting of cisplatin, chlorambucil, melphalan, methotrexate, fluracil, doxorubicin and bleomycin.

12. The method as defined in claim 1 in which the cytotoxic compound is a ribosome inactivating protein type 1 or type 2.

13. The method as defined in claim 1 in which the cytotoxic compound arrests protein synthesis within the cancer cell.

14. The method as defined in claim 1 in which the preserving agent prevents the collapse of a reactive center of the plasminogen activator inhibitor into the plasminogen activator inhibitor molecule.

15. The method as defined in claim 1 in which the coupling in step (A) is at a temperature of about 4° C. to 40° C. for a time of about 1 second to 78 hours.

16. A method of selectively delivering a cytotoxic compound into a cancer cell having on an outer surface thereof active binding sites for a reaction product, said binding sites including a lipoprotein-related protein, a urokinase plasminogen activator bound to a urokinase plasminogen activator receptor and combinations thereof, the method comprising the steps of:

A. coupling the cytotoxic compound to a plasminogen activator inhibitor selected from the group consisting of PAI-1 and PAI-2, modified with a preserving agent to provide the reaction product, the preserving agent preventing a collapse of a reactive center of the plasminogen activator inhibitor into the plasminogen activator inhibitor molecule thereby preserving the biological properties of the plasminogen activator inhibitor; and B. delivering the reaction product of step A to the outer surface of the cancer cell so as to form a complex with one or more of the outer surface binding sites, wherein the complex enters the cancer cell.

17. A method of selectively delivering a cytotoxic compound into a cancer cell having on an outer surface thereof active binding sites for a reaction product, said binding sites including a lipoprotein-related protein, a urokinase plasminogen activator bound to a urokinase plasminogen activator receptor and combinations thereof, the method comprising the steps of:

A. providing the reaction product including a plasminogen activator inhibitor selected from the group consisting of PAI-1 and PAI-2, and a cytotoxic compound, the plasminogen activator inhibitor having a reactive center incapable of collapsing into the plasminogen activator inhibitor molecule thereby preserving the biological properties of the plasminogen activator inhibitor; and B. delivering the reaction product of step A to the outer surface of the cancer cell so as to form a complex with one or more of the outer surface binding sites, wherein the complex enters the cancer cell.

* * * * *